US009269471B2

(12) United States Patent
Roessl et al.

(10) Patent No.: US 9,269,471 B2
(45) Date of Patent: Feb. 23, 2016

(54) DIFFERENTIAL PHASE-CONTRAST IMAGING WITH CIRCULAR GRATINGS

(75) Inventors: Ewald Roessl, Ellerau (DE); Thomas Koehler, Norderstedt (DE); Gerhard Martens, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 397 days.

(21) Appl. No.: 13/260,380

(22) PCT Filed: Mar. 15, 2010

(86) PCT No.: PCT/IB2010/051098
§ 371 (c)(1),
(2), (4) Date: Sep. 26, 2011

(87) PCT Pub. No.: WO2010/109368
PCT Pub. Date: Sep. 30, 2010

(65) Prior Publication Data
US 2012/0008747 A1 Jan. 12, 2012

(30) Foreign Application Priority Data

Mar. 27, 2009 (EP) .................................. 09156474

(51) Int. Cl.
*A61B 6/03* (2006.01)
*G21K 7/00* (2006.01)
*A61B 6/00* (2006.01)

(52) U.S. Cl.
CPC ................ *G21K 7/00* (2013.01); *A61B 6/4291* (2013.01); *A61B 6/484* (2013.01); *A61B 6/502* (2013.01)

(58) Field of Classification Search
CPC .... G01N 23/04; G01N 23/046; G01N 23/083
USPC ........................................................ 378/62, 2
See application file for complete search history.

(56) References Cited

U.S. PATENT DOCUMENTS

| 4,870,674 | A | 9/1989 | Schmahl et al. | |
|---|---|---|---|---|
| 7,394,890 | B1 * | 7/2008 | Wang et al. ..................... | 378/84 |
| 7,492,871 | B2 | 2/2009 | Popescu et al. | |
| 2001/0046276 | A1 * | 11/2001 | Schneider et al. .............. | 378/58 |
| 2004/0004176 | A1 | 1/2004 | Liang | |
| 2007/0183560 | A1 * | 8/2007 | Popescu et al. ................... | 378/5 |
| 2007/0183583 | A1 | 8/2007 | Baumann et al. | |
| 2010/0080436 | A1 | 4/2010 | Ohara | |

(Continued)

FOREIGN PATENT DOCUMENTS

| CN | 101011254 A | 8/2007 |
|---|---|---|
| JP | 2007206075 A | 8/2007 |

(Continued)

OTHER PUBLICATIONS

Pfeiffer et al, "Phase Retrieval and Differential Phase-Contrast Imaging With Low-Brilliance X-Ray Sources", Nature Physics, 2006,pp. 1-4.

*Primary Examiner* — Hoon Song

(57) ABSTRACT

An X-ray differential phase-contrast imaging system has three circular gratings. The circular gratings are aligned with the optical axis of the radiation beam and a phase stepping is performed along the optical axis with the focal spot, the phase grating and/or the absorber grating. The signal measured is the phase-gradient in radial direction away from the optical axis.

14 Claims, 3 Drawing Sheets

(56) References Cited

U.S. PATENT DOCUMENTS

2010/0220834 A1* 9/2010 Heismann et al. ............. 378/19
2012/0093297 A1* 4/2012 Kondoh ....................... 378/145

FOREIGN PATENT DOCUMENTS

| JP | 2008200361 A | 9/2008 |
| WO | 2008102598 A1 | 8/2008 |

* cited by examiner

DIFFERENTIAL PHASE-CONTRAST IMAGING WITH CIRCULAR GRATINGS

FIELD OF THE INVENTION

The invention relates to phase-contrast imaging. In particular, the invention relates to a phase-contrast imaging apparatus for examining an object of interest, a method of phase-contrast imaging, a computer-readable medium and a program element.

BACKGROUND OF THE INVENTION

For examination of objects of interest with electromagnetic radiation, visible or invisible light or X-rays may be used. The method disclosed in Pfeiffer et al. "Phase retrieval and differential phase-contrast imaging with low-brilliance X-ray sources", Nature Physics 2006 in the domain of X-ray differential phase-contrast imaging (DPC) is based on an extension of Talbot interferometry. The extension consists of adding a third grating allowing the use of a poly-chromatic X-ray spectrum. The gratings used in this technique are formed by linear trench arrangements, as depicted in FIGS. 1 and 2. The detection of intensity variations via phase stepping allows the measurement of the phase gradient of the X-ray wave front perpendicular to the trenches of the grating.

However, in order to provide for an image of reasonably well quality, an appropriate positioning accuracy while stepping and a non trivial phase retrieval may have to be performed.

SUMMARY OF THE INVENTION

It may be desirable to provide for an imaging system and method with a more robust possibility for phase retrieval.

The invention relates to a phase-contrast imaging apparatus for examining an object of interest, a method of phase-contrast imaging, a computer-readable medium and a program element according to the features of the independent claims. Further features of exemplary embodiments of the invention are stated in the dependent claims.

It should be noted that the features which are in the following described for example with respect to the imaging apparatus may also be implemented as method steps in the method, the computer-readable medium or the program element, and vice versa.

According to an exemplary embodiment of the invention, a phase-contrast imaging apparatus for examining an object of interest is provided, the apparatus comprising a source for emitting a beam of radiation, a detector and a phase grating positioned between the source and the detector. The detector is adapted for detecting the radiation after it has passed the object of interest and the phase grating, wherein the phase grating has a curved geometry.

For example, all gratings used in the imaging apparatus have such a curved geometry. The term "curved geometry" refers to a phase grating geometry which is not linear but comprises arcuated or bended structures, such as circles or segments of a circle or any.

According to another exemplary embodiment of the invention, the phase grating has one of a circular geometry and a spiral geometry. In other words, the phase grating (and for example both absorption gratings as well) comprise concentrically arranged trenches or a helical, i.e. spiral-like trench.

According to another exemplary embodiment of the invention, the beam of radiation emitted by the source is a cone-beam. Thus, the imaging apparatus is designed in cone-beam symmetry.

With the use of conventional X-ray tube sources, a linear grating arrangement breaks the cone-beam symmetry of the imaging system. The above and in the following described gratings respect the above-mentioned symmetry, thus yielding a couple of advantages.

For example, by using gratings with a curved geometry, for example spiral or circular gratings, the requirements on positioning accuracy while stepping may be reduced. Furthermore, phase retrieval may be simplified due to common-ground truth "phase point on the optical axis". Furthermore, the cylindrical symmetry may avoid edge distortions. The above and the in the following described setup may provide a viable alternative to other DPC techniques using linear gratings.

According to another exemplary embodiment of the invention, the imaging apparatus further comprises a second grating which is adapted in form of an absorption grating positioned in front of the detector. The second grating has a curved geometry as well and has a pitch different from the pitch of the first phase grating.

According to another exemplary embodiment of the invention, the imaging apparatus further comprises a third grating which is an absorption grating positioned between the source and the object of interest and which also has a curved geometry. The third grating has a third pitch which is different from the first pitch of the phase grating and allows for an essentially coherent illumination of the phase grating.

According to another exemplary embodiment of the invention, the imaging apparatus further comprises a stepper motor. The beam of radiation emitted by the source has an optical axis, wherein the stepper motor is adapted for moving at least one of the phase grating and the second (absorption) grating along the optical axis of the beam of radiation emitted by the source.

Furthermore, the imaging apparatus may be adapted in such a way that the focal spot of the beam of radiation emitted by the source moves along the optical axis during image acquisition.

According to another exemplary embodiment of the invention, the imaging apparatus further comprises a rotating motor, wherein the rotating motor is adapted for rotating at least one of the phase grating and the second grating around the optical axis of the beam of radiation.

For example, the phase grating G1 and/or the second absorption grating G2 are adapted in spiral geometry and positioned on the optical axis. Alternatively or additionally, one or each of the two gratings G1, G2 is positioned offset of the optical axis and rotated around the optical axis.

According to another exemplary embodiment of the invention, the pitch of the phase grating (104) is not constant but a function of a distance from the center of the phase grating. In particular, the pitch may increase with increasing distance from the center. This may be also the case for the absorption gratings G0 and G2. This may be useful to simplify the phase-stepping procedure along the optical axis.

According to another exemplary embodiment of the invention, the source is an X-ray source, wherein the apparatus is adapted as an X-ray based differential phase contrast imaging apparatus.

According to another exemplary embodiment of the invention, the source is a light source, wherein the imaging apparatus is adapted as an optical imaging apparatus where the beam of radiation used for probing the object is an optical radiation beam with a wavelength within the range of for example 400 to 1400 nm.

According to another exemplary embodiment of the invention, a method of phase-contrast imaging for examining an object of interest is provided, in which a beam of radiation is emitted by a source. Furthermore, a phase grating is positioned between the source and the detector. Phase stepping is performed along the optical axis with a focal spot, the phase grating and/or the absorber grating. Furthermore, radiation is detected by the detector after it has passed the object of interest and the phase grating, wherein the phase grating has a curved geometry.

According to another exemplary embodiment of the invention, a radial outward integration of the detected radiation is performed for phase retrieval.

According to another exemplary embodiment of the invention, at least one of the phase grating, a second grating, which is an absorption grating positioned in front of the detector and having a curved geometry, and a focal spot of the beam of radiation emitted by the source is moved along an optical axis of the beam.

According to another exemplary embodiment of the invention, at least one of the phase grating, the second grating and the beam of radiation emitted by the source is rotated around an optical axis of the beam.

According to another exemplary embodiment of the invention, a computer-readable medium is provided, in which a computer program for examination of an object of interest is stored which, when executed by a processor of an imaging apparatus causes the imaging apparatus to carry out the above-mentioned method steps.

According to another exemplary embodiment of the invention, a program element for examination of an object of interest is provided, which, when being executed by a processor of an imaging apparatus, causes the imaging apparatus to carry out the above-mentioned method steps.

It may be seen as a gist of the invention that three curved, for example circular or spiral-shaped gratings are used instead of three linear gratings for the DPC setup. In the case of linear gratings the phase stepping reveals the phase gradient along the Cartesian stepping direction. In the case of circular gratings aligned with the optical axis and thus respecting the cylindrical symmetry of the system, the phase stepping is performed along the optical axis with the focal spot, the phase grating or the absorber grating. The measured signal is the phase-gradient in the radial direction. The required positioning accuracy along the optical axis may be comparatively low compared to the relatively high accuracy required for the stepping in the case of linear gratings.

These and other aspects of the invention will become apparent from and elucidated with reference to the embodiments described hereinafter.

Exemplary embodiments of the invention will be described in following, with reference to the following drawings.

DETAILED DESCRIPTION OF EMBODIMENTS

Figure 1A:
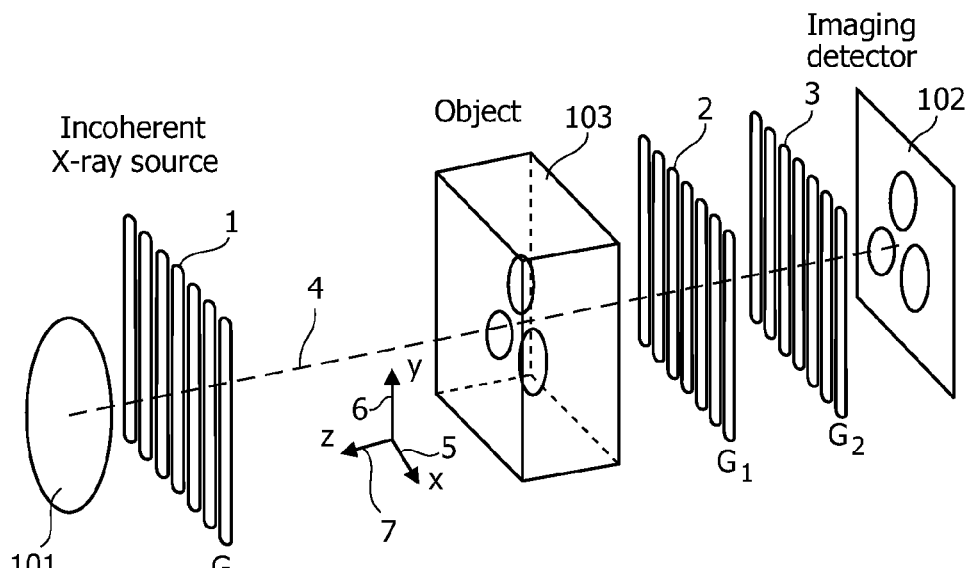
FIG. 1A shows a measurement setup with three linear gratings.

The illustration in the drawings is schematically and not to scale. In different drawings, similar or identical elements are provided with the same reference numerals.

FIG. 1A shows a measurement setup for differential phase-contrast imaging with linear gratings. An incoherent X-ray source is used which is symbolized by the focal spot 101. The radiation beam emitted by the source has an optical axis 4. First, the beam passes the absorption grating 1 ($G_0$). Then, the beam passes the object of interest 103 and then the phase grating 2 ($G_1$). After that, the beam passes a second absorption grating 3 ($G_2$), which is arranged before the imaging detector 102.

Reference numeral 5 depicts the x-axis, reference numeral 6 the y-axis and reference numeral 7 the z-axis, which is arranged parallel to the optical axis 4.

Figure 1B:
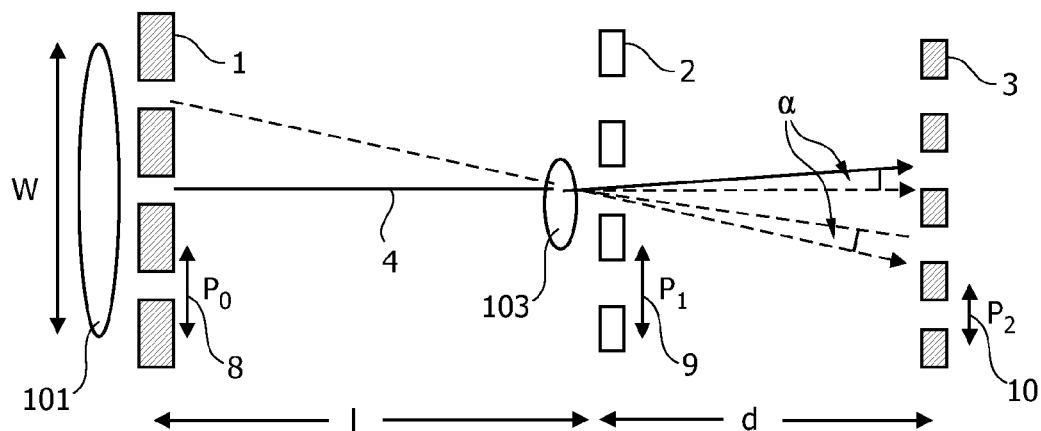
FIG. 1B shows a cross-sectional view of the setup of FIG. 1A.

FIG. 1B shows a cross-sectional view of the setup depicted in FIG. 1A. The focal spot of the source 101 has a width W, which is usually much bigger than the pitch $p_0$ of the first absorption grating 1 (see reference numeral 8). The phase grating 2 is arranged a distance 1 from the first absorption grating 1. Between the first absorption grating 1 and the phase grating 2 is the object of interest 103.

The second absorption grating 3 is arranged a distance d from the phase grating 2, which has a pitch 10 ($p_2$) which is smaller than the pitch of the first absorption grating 1. The phase grating 2 has a pitch 9 ($p_1$) which allows that radiation from the source which has a certain energy E produces a Talbot image at the imaging detector 102.

Figure 2A:
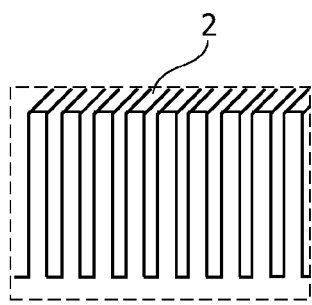
FIG. 2A shows a linear phase grating.
Figure 2B:
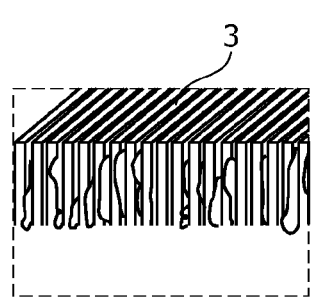
FIG. 2B shows a linear absorption grating.

FIGS. 2A and 2B each show a section of the linear gratings 2 and 3, respectively.

Figure 3:
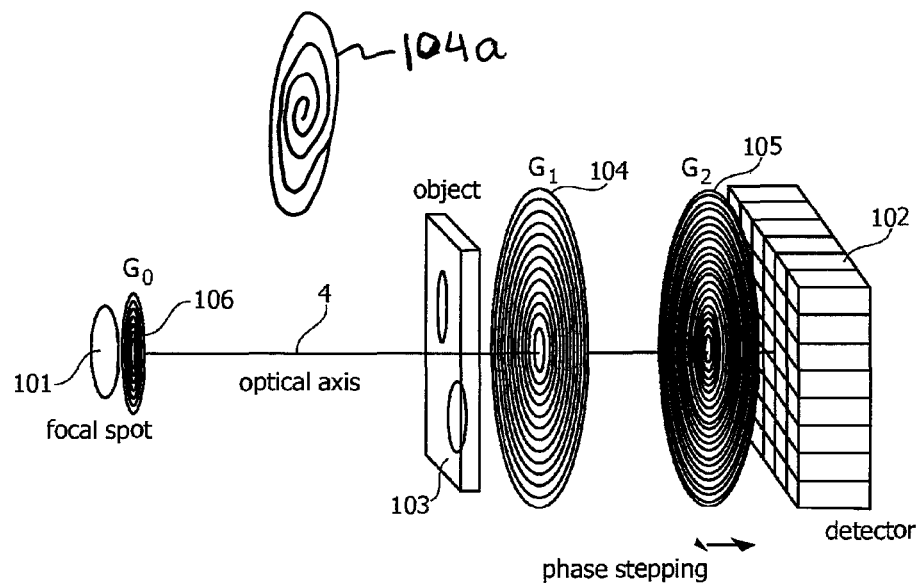
FIG. 3 shows a measurement setup according to an exemplary embodiment of the invention.

FIG. 3 shows a filter and detector setup for an imaging apparatus according to an exemplary embodiment of the invention. The imaging setup has three circular gratings, i.e. an absorption grating 106 arranged after the focal spot of the source 101, a phase grating 104 arranged after the object of interest 103 and a second absorption grating 105 arranged before the detector 102.

The second absorption grating 105 can be moved or stepped along the optical axis 4. It should be noted, that the pitches of the circular (or spiral 104a) gratings 104, 105 and 106 are not to scale.

With respect to the system disclosed by Pfeiffer et al. all linear gratings are replaced by circular gratings (or spiral gratings) and the phase stepping is performed along the optical axis. The method is sensitive to the radial phase gradient.

The relation between the pitch $p_1$ of $G_1$ and $p_2$ of $G_2$ remains unchanged. For a plane wave (synchrotron) $p2=p1/2$, for a spherical wave (as in the present case) $p2=p1/2*1/(1-d)$, with 1 being the distance between G0 and G1 and d the Talbot distance.

The source grating 106 is adapted to guarantee essentially "coherent" illumination of the phase grating 104. The distortions of the Talbot self-image (Fourier image) generated by the phase object 103 are analyzed by the absorption grating 105 through stepping along the optical axis 4. The detector measures the local phase-gradient in the radial direction. For phase-retrieval radial outward integrations are performed with the advantage of having a common "anchor" for the wave front phase.

According to another exemplary embodiment, the trenches of the gratings are not realized in the form of concentric rings but are realized as spirals. The phase stepping may then be implemented via a rotation of one of the gratings around the optical axis by an angle of 360 degrees.

It should be noted that a second phase grating (such as phase grating 410 of FIG. 4) may be positioned next to the first phase grating 104 in order to produce a second Talbot image at the detector.

It should also be noted, that the imaging system may either be an X-ray imaging system or an optical imaging system.

Figure 4:
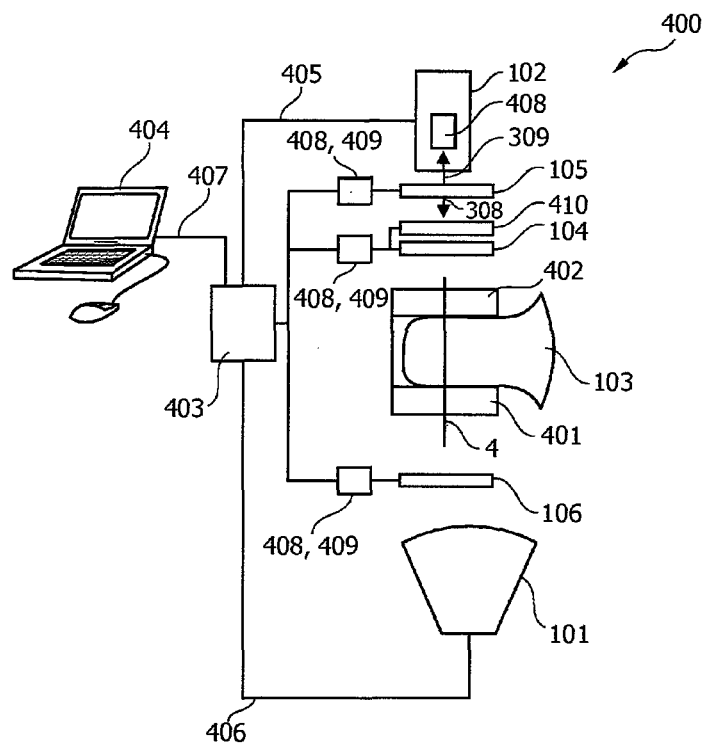
FIG. 4 shows an imaging system according to an exemplary embodiment of the invention.

FIG. 4 shows an imaging system 400 according to an exemplary embodiment of the invention. The imaging system depicted in FIG. 4 may be adapted in form of a mammography imaging system. The object of interest 103 may be a breast of a patient which is disposed between the two pressure plates 401, 402 for applying pressure to the patient's breast.

The source 101 may an X-ray source or, for instance, an optical energy source (in which case the system may be used for other purposes).

The radiation emitted by the source 101 first passes the grating 106 and then the object of interest to be imaged 103.

Then, the radiation passes a phase grating 104 and, if desired, a second phase grating 410. The phase gratings may be integrated in a corresponding housing and may thus form a module. The module is connected to the control unit 403 such that the gratings 104, 410 can be moved upwards and downwards along arrows 308, 309.

Furthermore, a second absorption grating 105 is positioned before the detector 102. Each of the gratings can be connected to the same or a respective individual motor 408 for moving the gratings along the arrows 308, 309 and/or for rotating the gratings around the optical axis 4.

Both the source 101 and the detector 102 are connected to the control unit 403 via lines 405, 406, respectively.

The detector 102 comprises a Talbot interferometer 408.

Furthermore, a data line 407 connects the control unit 403 to an input and output device 404, which can be used for inputting control information for controlling the imaging system 400 and which can also be used for outputting visual information relating to the final image.

Figure 5:
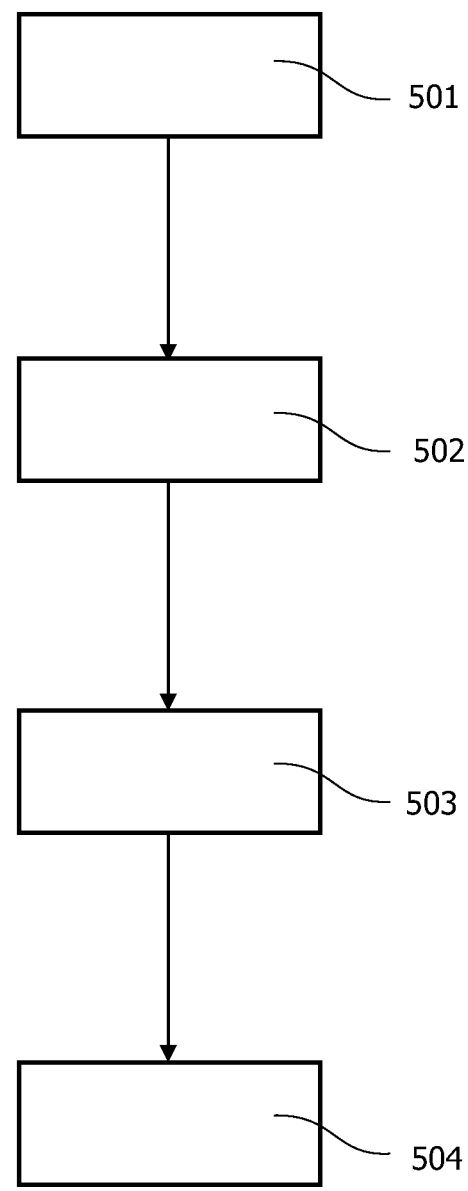
FIG. 5 shows a flow-chart of a method according to an exemplary embodiment of the invention.

FIG. 5 shows a flow-chart of a method according to an exemplary embodiment of the invention. In step 501 a beam of radiation is emitted by a source, for example an X-ray source emitting polychromatic x-rays. In step 502 focal spot, the phase grating or the absorption grating at the detector are stepped, i.e. moved along the optical axis. In case spiral gratings are used, a rotation is performed instead of the linear movement.

Then, in step 503 the radiation is detected after it has passed the object of interest and the gratings and in step 504 the phase is retrieved by performing radial outward integrations of the detected signal.

The integrations may also be started outside and heading inwards with a necessary condition to arrive at the same value on the optical axis.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

LIST OF REFERENCE SIGNS

1 Linear absorption grating
2 Linear phase grating
3 Linear absorption grating
4 Optical axis
5 x-axis
6 y-axis
7 z-axis
8 Pitch $p_0$
9 Pitch $p_1$
10 Pitch $p_2$
101 Source, focal spot
102 Detector
103 Object of interest
104 Phase grating $G_1$
105 Absorption grating $G_2$
106 Absorption grating $G_0$
400 Imaging system
401 First pressure plate
402 Second pressure plate
403 Control unit
404 Input and output unit
405 Connection line
406 Connection line
407 Connection line
408 Motor
409 Rotating motor
410 Second phase grating
501, 502, 503, 504 Method steps

The invention claimed is:

1. An x-ray based differential phase contrast imaging apparatus for examining an object, the apparatus comprising:
a source for emitting a beam of radiation having an optical axis;
a detector for detecting said beam of radiation; and
a plurality of gratings comprising an absorption grating positioned between the object and the detector and at least a phase grating positioned between the source and the detector,
wherein the phase grating comprises a spiral geometry.

2. The phase contrast imaging apparatus of claim 1, wherein the beam of radiation emitted by the source is a cone beam.

3. An x-ray based differential phase contrast imaging apparatus for examining an object, the apparatus comprising:
a source for emitting a beam of radiation having an optical axis;
a detector for detecting said beam of radiation; and
a plurality of gratings comprising an absorption grating positioned between the object and the detector and at least a phase grating positioned between the source and the detector,
wherein the absorption grating has a curved geometry and is rotatable around the optical axis.

4. An x-ray based differential phase contrast imaging apparatus for examining an object, the apparatus comprising:
a source for emitting a beam of radiation having an optical axis;
a detector for detecting said beam of radiation; and
a plurality of gratings comprising an absorption grating positioned between the source and the detector and at least a phase grating positioned between the source and the detector,
wherein the absorption grating has a curved geometry and is rotatable around the optical axis.

5. A phase contrast imaging apparatus for examining an object, the apparatus comprising:
a source for emitting a beam of radiation having an optical axis;
a detector for detecting said beam of radiation;
a plurality of gratings comprising an absorption grating positioned between the object and the detector and at least a phase grating positioned between the source and the detector; and a stepper motor configured to move the phase grating and another of the plurality of gratings along the optical axis of the beam of radiation emitted by the source, wherein the phase grating comprises a geometry selected from a circular geometry and a spiral geometry.

6. A phase contrast imaging apparatus for examining an object, the apparatus comprising:
   a source for emitting a beam of radiation having an optical axis;
   a detector for detecting said beam of radiation;
   a plurality of gratings comprising an absorption grating positioned between the object and the detector and at least a phase grating positioned between the source and the detector; and
   a rotating motor configured to rotate the phase grating and another of the plurality of gratings around the optical axis of the beam of radiation emitted by the source,
   wherein the phase grating comprises a geometry selected from a circular geometry and a spiral geometry.

7. The phase contrast imaging apparatus of claim 1, wherein a pitch of the phase grating increases with increasing distance from a center of the phase grating.

8. A method of phase contrast imaging for examining an object, the method comprising the acts of:
   emitting a beam of radiation having an optical axis from a source;
   detecting said beam of radiation by a detector;
   positioning a plurality of gratings comprising an absorption grating between the object and the detector and at least a phase grating between the source and the detector; and
   detecting, by the detector, the beam of radiation after passing the object and the phase grating,
   wherein the phase grating comprises a spiral geometry.

9. The method of claim 8, further comprising the act of performing one of a radial outward integration and a radial inward integration of the detected radiation for phase retrieval.

10. A method of x-ray based differential phase contrast imaging for examining an object, the method comprising the acts of:
    emitting a beam of radiation having an optical axis by a source;
    detecting said beam of radiation by a detector;
    positioning a plurality of gratings comprising an absorption grating between the object and the detector and at least a phase grating between the source and a detector;
    detecting, by the detector, the beam of radiation after passing the object and the grating; and
    rotating at least one of the phase grating having a geometry selected from a circular geometry and a spiral geometry and another of the plurality of gratings and the beam of radiation emitted by the source around an optical axis of the beam,
    wherein the absorption grating has a pitch which is different from a pitch of the phase grating.

11. A non-transitory computer-readable medium comprising a computer program for examination of an object which, when executed by a processor of an imaging apparatus, performs a method of x-ray based differential phase contrast imaging for examining the object, the method comprising the acts of:
    emitting, from a source, a beam of radiation having an optical axis;
    detecting said beam of radiation by a detector;
    positioning a plurality of gratings comprising an absorption grating between the object and the detector and at least a phase grating between the source and a detector; and
    detecting, by the detector, the beam of radiation after passing the object of interest and the phase grating;
    wherein the phase grating comprises a spiral geometry.

12. The non-transitory computer-readable of claim 11, wherein the method further comprises the act of rotating at least one of the phase grating, a second grating of the plurality of gratings, and the beam of radiation around the optical axis.

13. The phase contrast imaging apparatus of claim 3, wherein the absorption grating has a pitch which is different from a pitch of the phase grating.

14. The phase contrast imaging apparatus of claim 4, wherein the absorption grating has a pitch which is different from a pitch of the phase grating and allows for an essentially coherent illumination of the phase grating.

* * * * *